United States Patent [19]

Takemoto et al.

[11] Patent Number: 4,740,616

[45] Date of Patent: Apr. 26, 1988

[54] PROCESS FOR THE PRODUCTION OF AN N-PROTECTED-L-α-ASPARTYL-L-PHENYLALANINE

[75] Inventors: Tadashi Takemoto; Toshihide Yukawa; Kunio Hisamitsu, all of Kawasaki, Japan

[73] Assignee: Ajinomoto Co., Inc., Tokyo, Japan

[21] Appl. No.: 883,354

[22] Filed: Jul. 1, 1986

[30] Foreign Application Priority Data

Jul. 1, 1985 [JP] Japan ................... 60-144137

[51] Int. Cl.$^4$ .......................................... C07C 101/20
[52] U.S. Cl. ..................................... 562/448; 530/801
[58] Field of Search .................... 530/801; 562/448

[56] References Cited

U.S. PATENT DOCUMENTS

| | | | |
|---|---|---|---|
| 3,808,190 | 4/1974 | Dahlmans et al. | 560/40 |
| 3,833,553 | 9/1974 | Ariyashi et al. | 530/801 |
| 3,833,554 | 9/1974 | Ariyashi et al. | 530/801 |
| 3,879,372 | 4/1975 | Boesten | 530/801 |
| 3,933,781 | 1/1976 | Bachman et al. | 530/801 |
| 3,962,207 | 6/1976 | Uchiyama et al. | 530/801 |
| 4,017,472 | 4/1977 | Farkas et al. | 530/801 |
| 4,333,872 | 6/1982 | Sampathkumar et al. | 530/801 |
| 4,507,231 | 3/1985 | Gourbault | 530/801 |
| 4,539,147 | 9/1985 | Filippini et al. | 530/801 |

OTHER PUBLICATIONS

Pavlova et al., Russian Chem. Revs., vol. 80, pp. 316–323 (1981).
Albini et al., Chem. & Ind., pp. 484–485 (1985).

*Primary Examiner*—James H. Reamer
*Attorney, Agent, or Firm*—Oblon, Fisher, Spivak, McClelland & Maier

[57] ABSTRACT

A process is described for the synthesis of N-protected-L-α-aspartyl-L-phenylalanine by both (a) the reaction of an N-protected-L-aspartic anhydride and a $R_1$-L-phenylalanine, and (b) the reaction of an N-protected-L-aspartic anhydride and L-phenylalanine in an aqueous medium in the presence of $R_2$, where $R_1$ may be an alkali metal salt, alkaline earth metal salt, ammonium salt or organic amine salt, and $R_2$ may be an ammonium salt or an alkali or alkaline earth metal salt of an inorganic or organic acid.

21 Claims, No Drawings

PROCESS FOR THE PRODUCTION OF AN N-PROTECTED-L-α-ASPARTYL-L-PHENYLALANINE

DETAILED DESCRIPTION OF THE INVENTION

The present invention relates to a process for the production of an N-protected-L-α-aspartyl-L-phenylalanine and an improvement thereof. More specifically, it relates to (a) a process for the production of an N-protected-L-α-aspartyl-L-phenylalanine which is characterized by reacting an N-protected-L-aspartic anhydride and an alkali metal salt, alkaline earth metal salt, ammonium salt or organic amine salt of L-phenylalanine in an aqueous medium (the basic process) and (b) a method of producing an N-protected-L-α-aspartyl-L-phenylalanine, which comprises reacting an N-protected-L-aspartic anhydride with L-phenylalanine in an aqueous medium at a pH not lower than 7 in the presence of ammonium salt or a salt of an alkali or alkaline earth metal of an inorganic or organic acid (the improved process).

L-α-Aspartyl-L-phenylalanine methyl ester is known as an excellent sweetener, and a number of processes for its production are known. For example, it is known that an N-protected-L-α-aspartyl-L-phenylalanine may easily be converted to L-α-aspartyl-L-phenylalanine methyl ester by known techniques (Japanese Patent Application Laid-open Nos. 82752/1978 and 219258/1984). Therefore, if it is possible to obtain such an N-protected-L-α-aspartyl-L-phenylalanine in a high yield by a simple process, then it will be extremely advantageous as an industrial process for the production of L-α-aspartyl-L-phenylalanine methyl ester.

Heretofore, as the process for the production of an N-protected-L-α-aspartyl-L-phenylalanine, a process which comprises reacting L-phenylalanine with an N-protected-L-aspartic anhydride (Japanese Patent Publication No. 26133/1980), was known. But since this process involved a reaction in acetic acid, which is an organic solvent and has strong corrosive properties, it was not completely satisfactory as an industrial production process because of the necessity of a device for separating and recovering the solvent and also from an aspect of the corrosion of the device material.

Under such circumstances, the present inventors have been intensively studying in search of a process for the production of an N-protected-L-α-aspartyl-L-phenylalanine which does not suffer from such drawbacks described above. They have now surprisingly discovered that by reacting an alkali metal salt, alkaline earth metal salt or organic amine salt of L-phenylalanine with an N-protected-L-aspartic anhydride in an aqueous medium, an N-protected-L-α-aspartyl-L-phenylalanine salt may be obtained in a high yield, thereby having accomplished the present invention (the basic process).

The basic process will be explained in detail first.

The N-protected-L-α-aspartyl-L-phenylalanine salt produced in the reaction mixture in the present invention may be converted to an N-protected-L-α-aspartyl-L-phenylalanine by neutralization with an acid.

Further, as shown in Comparative Example 1 described hereinafter, in an aqueous medium in which L-phenylalanine does not form a salt, the L-phenylalanine undergoes substantially no reaction with the N-protected-L-aspartic anhydride but is left as the unreacted L-phenylalanine for recovery, and therefore the novelty of the reaction of the L-phenylalanine salt and the N-protected-L-aspartic anhydride is distinct. In this connection, that the L-phenylalanine is reacted in the form of its salt with the N-protected-L-aspartic anhydride in the aqueous medium is presumed more essentially to be that the L-phenylalanine is reacted in the form of an L-phenylalaninate ion

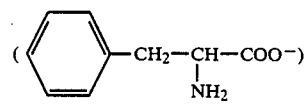

with the N-protected-L-asparatic anhydride. For example, in Example 1 described hereinlater, the reason why the pH of the reaction mixture is maintained at 12.0–12.5 with an NaOH aqueous solution, although a nearly equimolar amount of an N-protected-L-aspartic anhydride is firstly added to L-phenylalanine sodium salt monohydrate, is because otherwise the hydrogen ion of a free β-carboxyl group generated on the aspartic acid residue of the N-protected-L-α-aspartyl-L-phenylalanine produced by the reaction would be replaced by the Na+ ion of the L-phenylalanine sodium salt and the unreacted L-phenylalaninate ion would be converted to a non-charged L-phenylalanine

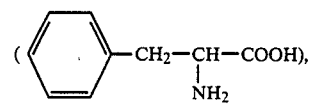

thus preventing smooth progress of the reaction.

As the protecting group of the N-protected-L-aspartic anhydride used in the process of this invention, there may be used protecting groups used for the conventional peptide synthesis, for example, formyl, acetyl, benzyloxycarbonyl, t-butoxycarbonyl, 1-methyl-2-acetylvinyl, acetoacetyl groups etc., of which the formyl group is suitably used.

Examples of the alkali metal salt of L-phenylalanine suitably used in the present invention include sodium, potassium and lithium salts of L-phenylalanine; examples of the alkaline earth metal salt include the magnesium and calcium salts; and examples of the organic amine salt include tertiary amine salts, e.g. tributylamine, triethylamine, trimethylamine etc. salts of L-phenylalanine. Further, it is needless to say that the alkali metal salts, alkaline earth metal salts and organic amine salts of L-phenylalanine may also be produced in situ in the reaction mixture by reacting the L-phenylalanine with sodium hydroxide, potassium hydroxide, calcium hydroxide, magnesium hydroxide, tributylamine etc., respectively.

As the solvent used in the present invention, water or a mixture of water with an organic solvent may be used. Although there is no particular restriction on such an organic solvent as long as it does not unduly react with the starting materials and the reaction product, alcohols such as methanol, ethanol etc., esters such as ethyl acetate, methyl acetate etc., ketones such as acetone, methyl ethyl ketone etc., ethers such as tetrahydrofuran, dioxane etc., amines such as dimethylformamide, diacetylamide etc., and aromatic hydrocarbons such as toluene etc. may be used.

The reaction temperature is suitably 30° C. to 80° C., more preferably 20° C. to 60° C. in view of the hydrolysis of the N-protected-L-aspartic anhydride.

While there is no particular restriction on the reaction time, since the reaction rate between the N-protected-L-aspartic anhydride and the L-phenylalanine salt is great and hence there is no need to conduct the reaction for a prolonged time, the reaction is generally brought to completion within 2 hours after the completion of mixing of the starting materials although it depends on the reaction temperature.

The molar ratio of the N-protected-L-aspartic anhydride and L-phenylalanine salt used may be in the range of 0.5 to 3.0 more preferably 0.8 to 2.0 in some cases, the lower the concentration of the L-phenylalanine salt, the better the reaction yield, and in such cases, by appropriately adjusting the pH value of the reaction medium to 7 or higher, any desired concentration of the L-phenylalanine salt may be obtained.

Since the N-protected-L-$\alpha$-aspartyl-L-phenylalanine is obtained in the form of its alkali metal salt, alkaline earth metal salt, ammonium salt or organic amine salt by the present invention, it may be neutralized with an acid such as hydrochloric acid, sulfuric acid etc. and thereafter crystallized to obtain a crystalline N-protected-L-$\alpha$-aspartyl-L-phenylalanine, or alternatively it may be used as such in a solution form without isolation in the conversion reaction to L-$\alpha$-aspartyl-L-phenylalanine methyl ester.

The following examples will be given for further description, but it should be noted that the embodiments of the present invention are not restricted thereto.

EXAMPLE 1

12.4 g (0.060 mole) of L-phenylalanine sodium salt monohydrate was dissolved in 65 ml of water, and cooled to 5° C. 9.5 g (0.066 mole) of N-formyl-L-aspartic anhydride was added thereto with stirring at the same temperature over an hour. During that time, the pH of the reaction mixture was maintained at 12.0–12.5 with a 4N NaOH aqueous solution.

Thereafter, the N-formyl-L-$\alpha$-aspartyl-L-phenylalanine (hereinafter simply referred to as For-$\alpha$-AP) in the reaction mixture was quantitatively analyzed by HPLC (High performance Liquid Chromatography), to find that it had been formed in a Yield of 68.2% based on the L-phenylalanine sodium salt monohydrate. In addition, 30.0% of N-formyl-L-$\beta$-aspartyl-L-phenylalanine (For-$\beta$-AP), etc. had been by-produced.

EXAMPLE 2

9.9 g (0.060 mole) of L-phenylalanine and 2.4 g (0.060 mole) of NaOH were dissolved in 65 ml of water, and cooled to 5° C. With stirring at the same temperature, 9.5 g (0.066 mole) of N-formyl-L-aspartic anhydride was added thereto over 40 minutes. During that time, the pH of the reaction mixture was maintained at 12.0–12.5 by adding a 4N NaOH aqueous solution. Thereafter, the For-$\alpha$-AP in the reaction mixture was quantitatively analyzed to find that it had been produced in a yield of 68.5% based on the L-phenylalanine, while the For-$\beta$-AP in a yield of 30.4%.

EXAMPLE 3

9.9 g (0.060 mole) of L-phenylalanine was suspended in 80 ml of water, and, after adjusting the pH to 8.0 with a 4N NaOH aqueous solution, cooled to 5° C. With stirring at the same temperature, 9.9 g (0.069 mole) of N-formyl-L-aspartic anhydride was added thereto over an hour. During that time, the pH of the reaction mixture was maintained at 8.0–8.5 by adding a 4N NaOH aqueous solution.

Thereafter, the For-$\alpha$-AP was quantitatively analyzed by HPLC, to find that it had been produced in a yield of 66.6% based on the L-phenylalanine, while the For-$\beta$-AP in a yield of 33.1%.

EXAMPLE 4

The reaction was conducted under the same conditions as in Example 3 except the pH. That is, the pH at the start of the reaction was pH=10.0, and during the reaction, the pH was maintained at 10.0–10.5.

The yield of the For-$\alpha$-AP was 67.2% based on the L-phenylalanine, while the For-$\beta$-AP in a yield of 32.0%.

EXAMPLE 5

9.9 g (0.060 mole) of L-phenylalanine was suspended in 80 ml of water, and, after adjusting the pH to 8.0 with a 4N NaOH aqueous solution, cooled to 5° C. With stirring at the same temperature, 9.9 g (0.069 mole) of N-formyl-L-aspartic anhydride was added. Thereafter, the pH was maintained at 8.0–8.5 for 15 minutes by adding a 4N NaOH aqueous solution.

The For-$\alpha$-AP in the reaction mixture was quantitatively analyzed by HPLC, to find that it had been produced in a yield of 55.1% based on the L-phenylalanine, while the For-$\beta$-AP in a yield of 30.0%.

EXAMPLE 6

A reaction was conducted at room temperature under the same conditions as in Example 1. The yield of the For-$\alpha$-AP was 56.2% based on the L-phenylalanine monosodium salt monohydrate, while the For-$\beta$-AP in a yield of 27.7%.

EXAMPLE 7

9.9 g (0.060 mole) of L-phenylalanine and 3.2 g (0.030 mole) of sodium carbonate were dissolved in 90 ml of water. With stirring at 10° C., 9.5 g (0.066 mole) of N-formyl-L-aspartic anhydride was added thereto over 40 minutes. During that time, the pH of the reaction mixture was maintained at 8.0–8.5 by adding a 10% sodium carbonate aqueous solution.

Thereafter, the For-$\alpha$-AP in the reaction mixture was quantitatively analyzed to find that it had been produced in a yield of 55.3% based on the L-phenylalanine, while the For-$\beta$-AP in a yield of 26.7%.

EXAMPLE 8

9.9 g (0.060 mole) of L-phenylalanine and 2.4 g of NaOH were dissolved in a mixed solvent of 40 ml of water and 40 ml of methanol, and thereafter cooled to −10° C. With stirring at the same temperature, 9.5 g (0.066 mole) of N-formyl-L-aspartic anhydride was added thereto over an hour. During that time, the pH was maintained at 12.0–12.5 with a 4N NaOH aqueous solution.

Thereafter, the For-$\alpha$-AP in the reaction mixture was quantitatively analyzed by HPLC to find that it had been produced in a yield of 57.5% based on the L-phenylalanine, while the For-$\beta$-AP in a yield of 28.0%.

EXAMPLE 9

9.9 g (0.060 mole) of L-phenylalanine and 3.4 g (0.060 mole) of KOH were dissolved in 65 ml of water, and cooled to 5° C. With stirring at the same temperature, 7.9 g (0.055 mole) of N-formyl-L-aspartic anhydride was added thereto over an hour. During that time, the pH of the reaction mixture was maintained at 12.0–12.5 by adding a 4N KOH aqueous solution. The For-α-AP in the reaction mixture had been produced in a yield of 67.8% based on the N-formyl-L-aspartic anhydride, while the For-β-AP in a yield of 29.0%.

EXAMPLE 10

9.9 g (0.060 mole) of L-phenylalanine and 6.1 g (0.060 mole) of triethylamine were dissolved in 65 ml of water, and cooled to 5° C. With stirring at the same temperature, 10.4 g (0.066 mole) of N-acetyl-L-aspartic anhydride was added thereto over 30 minutes. During that time, the pH of the reaction mixture was maintained at 8.0–8.5 by adding triethylamine.

The N-acetyl-L-α-aspartyl-L-phenylalanine (Ac-α-AP) in the reaction mixture had been produced in a yield of 52.1% based on the L-phenylalanine, while the N-acetyl-L-β-aspartyl-L-phenylalanine (Ac-βAP) in a yield of 28.9%.

EXAMPLE 11

12.4 g (0.060 mole) of L-phenylalanine sodium salt monohydrate was dissolved in 65 ml of water, and cooled to 5° C. To this was added a suspension of 17.2 g (0.069 mole) of N-benzyloxycarbonyl-L-aspartic anhydride dispersed in 40 ml of toluene with stirring at the same temperature, and the reaction was effected over an hour. During that time, the pH of the reaction mixture was maintained at 10.0–10.5.

After phase separation, the N-benzyloxycarbonyl-L-α-aspartyl-L-phenylalanine (Z-α-AP) in the aqueous phase was quantitatively analyzed by HPLC, to find that it had been produced in a yield of 67.9% based on the L-phenylalanine, while the N-benzyloxycarbonyl-L-β-aspartyl-L-phenylalanine (Z-β-AP) in a yield of 31.3%.

COMPARATIVE EXAMPLE 1

9.9 g (0.060 mole) of L-phenylalanine was suspended in 65 ml of water, and cooled to 5° C. With stirring at the same temperature, 9.5 g (0.006 mole) of N-formyl-L-aspartic anhydride was added thereto, and stirred for 30 minutes.

The insoluble crystals were dissolved by adding a 4N NaOH aqueous solution, and analyzed by HPLC, but no For-α-AP was detected. Instead, what had been detected were N-formyl-L-aspartic acid and the unreacted L-phenylalanine.

Since the basic process has been explained hereinbefore, the improved process of the present invention will be explained in great detail hereinafter.

Although the basic process of the present invention is free from the above-mentioned prior-art disadvantages, it is not satisfactory in the yield of N-protected-L-α-aspartyl-L-phenylalanines since an N-protected-L-β-aspartyl-L-phenylalanine is formed as a by-product together with the desired α-aspartyl derivative, and the formation of the by-product, i.e., the β-aspartyl derivative, could not be sufficiently suppressed. In view of the above, the inventors have conducted extensive investigations so as to suppress the formation of N-protected-L-β-aspartyl-L-phenylalanines, in other words, to increase the ratio of N-protected-L-α-aspartyl-L-phenylalanines to N-protected-L-β-aspartyl-L-phenylalanines (hereinafter referred to as the α/β ratio).

To their surprise it has now been found that the formation of N-protected-L-β-aspartyl-L-phenylalanines can be suppressed and the N-protected-L-α-aspartyl-L-phenylalanines can be produced in high yields by reacting an N-protected-L-aspartic anhydride with L-phenylalanine in an aqueous medium in the presence of a salt of an alkali or alkaline earth metal of an inorganic or organic acid. This improved process has been accomplished based on the above finding.

The improved process is substantially the same as the basic process except the presence of a salt of an alkali or alkaine earth metal of an inorganic or organic acid in the reaction medium.

Examples of suitable salts of alkali or alkaline earth metals to be used include inorganic salts, such as sodium chloride, potassium chloride and calcium chloride; and organic salts, such as sodium acetate and potassium acetate. There is no particular limitation on the amount of the salt to be used. However, they are usually employed in an amount from 0.5 to 20 times, by mole, preferably from 1 to 10 times, by mole, that of the N-protected-L-aspartic anhydride or L-phenylalanine.

The pH of the reaction mixture can be at any value not lower than 7.0. The pH adjustment can be carried out with the use of the hydroxide or carbonate of an alkali metal or alkaline earth metal or an organic amine.

The improved process of the present invention will further be illustrated by way of examples. It would, however, be understood that the invention is not limited thereto.

EXAMPLE 12

In 65 ml. of water were dissolved 12.4 g. (0.060 mol.) of L-phenylalanine sodium salt monohydrate and 17.6 g. (0.300 mol.) of sodium chloride. The resulting solution was cooled to −20° C. and, at the same temperature, 9.5 g. (0.066 mol.) of N-formyl-L-aspartic anhydride was added thereto with stirring over a period of 1 hour, during which the pH of the reaction mixture was maintained in the range of from 12.0 to 12.5 by the addition of an aqueous 4N NaOH solution.

Thereafter, the amount of For-α-AP contained in the resulting reaction mixture was determined by means of HPLC.

The yield of the For-α-AP was 73.5%, based on the L-phenylalanine sodium salt monohydrate. In addition to the For-α-AP, For-β-AP was yielded as a by-product in a 24.3% yield.

EXAMPLE 13

In 65 ml. of water were added 9.9 g. (0.060 mol.) of L-phenylalanine and 2.4 g. (0.060 mol.) of NaOH. To this solution was added 17.6 g. (0.300 mol.) of sodium chloride. The resulting solution was cooled to 31 20° C., and 9.5 g. (0.066 mol.) of N-formyl-L-aspartic anhydride was added thereto with stirring over a period of 1 hour, during which the pH of the reaction mixture was maintained in the range of from 12.0 to 12.5 by the addition of an aqueous 4N NaOH solution.

Thereafter, the amount of For-α-AP contained in the reaction mixture was determined by means of HPLC. The yield of the For-α-AP was 73.5%, based on the L-phenylalanine. For-β-AP was yielded as a by-product in a 24.5% yield.

EXAMPLE 14

In 50 ml. of water was suspended 9.9 g. (0.060 mol.) of L-phenylalanine. The pH of the mixture was adjusted to 12.0 by the addition of an aqueous 4N NaOH solution, and 17.6 g. (0.300 mol.) of sodium chloride was added thereto. The resulting mixture was then cooled to −20° C., and 9.9 g. (0.069 mol.) of N-formyl-L-aspartic anhydride was added thereto with stirring over a period of 1 hour, during which the pH of the reaction mixture was maintained in the range of from 12.0 to 12.5 by the addition of an aqueous 4N NaOH solution.

Thereafter, the amount of For-$\alpha$-AP contained in the reaction mixture was determined by means of HPLC. The yield of the For-$\alpha$-AP was 73.2%, based on the L-phenylalanine. For-$\beta$-AP was yielded as a by-product in a 24.4% yield.

EXAMPLE 15

In 80 ml. of water was suspended 9.9 g. (0.060 mol.) of l-phenylalanine, and 22.4 g. (0.300 mol.) of potassium chloride was added thereto. The pH of the mixture was adjusted to 12.0 by the addition of an aqueous 4N NaOH solution. The resulting mixture was cooled to −10° C., and 9.5 g. (0.066 mol.) of N-formyl-L-aspartic anhydride was added thereto with stirring over a period of 40 minutes, during which the pH of the reaction mixture was maintained in the range of from 12.0 to 12.5 by the addition of a 4N NaOH solution.

Thereafter, the amount of For-$\alpha$-AP contained in the reaction mixture was determined by means of HPLC. The yield of the For-$\alpha$-AP was 74.4%, based on the L-phenylalanine. For-$\beta$-AP was yielded as a by-product in a 23.9% yield.

EXAMPLE 16

In 80 ml. of water was suspended 9.9 g. (0.060 mol.) of L-phenylalanine, and 24.6 g. (0.300 mol.) of sodium acetate was added thereto, The pH of the mixture was adjusted to 12.0. The resulting mixture was cooled to 5° C., and 9.5 g. (0.066 mol.) of N-formyl-L-aspartic anhydride was added thereto with stirring over a period of 1 hour, during which the pH of the reaction mixture was maintained in the range of from 12.0 to 12.5 by the addition of a 4N NaOH solution.

Thereafter, the amount of For-$\alpha$-AP contained in the reaction mixture was determined by means of HPLC. The yield of the For-$\alpha$-AP was 71.3%, based on the L-phenylalanine. For-$\beta$-AP was yielded as a by-product in a 26.4% yield.

EXAMPLE 17

In 50 ml. of water was suspended 9.9 g. (0.060 mol.) of L-phenylalanine, and 17.6 g. (0.300 mol.) of sodium chloride was added thereto. The pH of the suspension was adjusted to 10.0 by the addition of a 4N NaOH solution. The resulting mixture was cooled to −20° C., and 9.5 g. (0.066 mol.) of N-formyl-L-aspartic anhydride was added thereto with stirring over a period of 1 hour, during which the pH of the reaction mixture was maintained in the range of from 10.0 to 10.5 by the addition of a 4N NaOH solution.

Thereafter, the amount of For-$\alpha$-AP contained in the reaction mixture was determined by means of HPLC. The yield of the For-$\alpha$-AP was 71.5%, based on the L-phenylalanine. For-$\beta$-AP was yielded as a by-product in a 26.3% yield.

EXAMPLE 18

In 50 ml. of water was suspended 9.9 g. (0.060 mol.) of L-phenylalanine, and 13.4 g. (0.018 mol.) of potassium chloride was added thereto. The pH of the mixture was adjusted to 12.0 by the addition of a 4N NaOH solution. The resulting mixture was cooled to −15° C., and 9.5 g. (0.066 mol.) of N-formyl-L-aspartic anhydride was added thereto with stirring over a period of 1 hour, during which the pH of the reaction mixture was maintained in the range of from 12.0 to 12.5 by the addition of a 4N NaOH solution.

Thereafter, the amount of For-$\alpha$-AP contained in the reaction mixture was determined by means of HPLC. The yield of the For-$\alpha$-AP was 71.9%, based on the L-phenylalanine. For-$\beta$-AP was yielded as a by-product in a 25.2% yield.

EXAMPLE 19

In 65 ml. of water was suspended 9.9 g. (0.060 mol.) of L-phenylalanine, and 17.6 g. (0.300 mol.) of sodium chloride was added thereto. The pH of the mixture was adjusted to 12.0 by the addition of a 4N NaOH solution. The resulting mixture was cooled to −20° C., and 16.4 g. (0.066 mol.) of N-benzyloxycarbonyl-L-aspartic anhydride was added thereto with stirring over a period of 1 hour, during which the pH of the reaction mixture was maintained in the range of from 12.0 to 12.5. by the addition of a 4N NaOH solution.

Thereafter, the amount of Z-$\alpha$-AP contained in the reaction mixture was determined by means of HPLC. The yield of the $\alpha$-aspartyl derivative was 72.6%, based on the L-phenylalanine. Z-$\beta$-AP was yielded as a by-product in a 24.5% yield.

EXAMPLE 20

In 65 ml. of water was suspended 9.9 g. (0.060 mol.) of L-phenylalanine, and 17.6 g. (0.300 mol.) of sodium chloride was added thereto. The pH of the mixture was adjusted to 12.0 by the addition of a 4N NaOH solution. The resulting mixture was cooled to −20° C., and 10.4 g. (0.066 mol.) of N-acetyl-L-aspartic anhydride was added thereto with stirring over a period of 1 hour, during which the pH of the reaction mixture was maintained in the range of from 12.0 to 12.5.

Thereafter, the amount of Ac-$\alpha$-AP was determined by means of HPLC. The yield of the $\alpha$-aspartyl derivative was 63.2%, based on the L-phenylalanine. Ac-$\beta$-AP was yielded as a by-product in a 21.3% yield.

EXAMPLE 21

In a mixture of 50 ml. of water and 15 ml. of methanol was suspended 9.9 g. (0.060 mol.) of L-phenylalanine, and 17.6 g. (0.300 mol.) of sodium chloride was added thereto. The pH of the mixture was adjusted to 12.0 by the addition of a 4N NaOH solution. The resulting mixture was cooled to −20° C., and 9.5 g. (0.066 mol.) of N-formyl-L-aspartic anhydride was added thereto with stirring over a period of 1 hour, during which the pH of the reaction mixture was maintained in the range of from 12.0 to 12.5

Thereafter, the amount of For-$\alpha$-AP was determined by means of HPLC. The yield of the For-$\alpha$-AP was 65.3%, based based on the L-phenylalanine. For-$\beta$-AP was yielded as a by-product in a 23.3% yielded.

What is claimed is:

1. A process for producing an N-protected-L-$\alpha$-aspartyl-L-phenylalanine compound, comprising:
reacting an N-protected-L-aspartic anhydride with L-phenylalanine in an aqueous medium at a pH not lower than 7 in the presence of an ammonium salt, an alkali salt of an inorganic acid, an alkali salt of an organic acid, an alkaline earth metal salt of an inorganic acid, or an alkaline earth metal salt of an organic acid to obtain an N-protected-L-α-aspartyl-L-phenylalanine salt.

2. The process of claim 1, wherein said N-protected-L-α-aspartyl-L-phenylalanine salt is treated with an acid to obtain an N-protected-L-α-aspartyl-L-phenylalanine.

3. The process of claim 1, wherein the N-protected-L-α-aspartyl-L-phenylalanine possess as a protecting group, a formyl group, an acetyl group, a benzyloxycarbonyl group, a t-butoxycarbonyl group, a 1-methyl-2-acetylvinyl group, or an acetoacetyl group.

4. The process of claim 1, wherein said alkali metal is sodium, potassium or lithium.

5. The process of claim 1, wherein said alkaline earth metal is magnesium or calcium.

6. The process of claim 1, wherein said ammonium salt is ammonium chloride.

7. The process of claim 1, wherein said aqueous medium is water or a mixture of water with an organic solvent.

8. The process of claim 7, wherein said organic solvent is an alcohol, an ester, a ketone, an ether, an amine or an aromatic hydrocarbon.

9. The process of claim 8, wherein said organic solvent is methanol, ethanol, ethyl acetate, methyl acetate, acetone, methylethylketone, tetrahydrofuran, dioxane, dimethylformamide, diacetylamide, or toluene.

10. The process of claim 1, wherein said reaction is conducted at a temperature of from −30° C. to 80° C.

11. The process of claim 1, wherein said reaction is conducted at a temperature of from −20° C. to 60° C.

12. The process of claim 1, wherein said N-protected-L-aspartic anhydride and said L-phenylalanine are used in a molar ratio of from 0.5 to 3.0.

13. The process of claim 12, wherein said ratio is 0.8 to 2.0.

14. The process of claim 1, wherein the reaction is run in the presence of sodium chloride, potassium chloride, calcium chloride, sodium acetate or potassium acetate.

15. The process of claim 14, wherein sodium chloride, potassium chloride or calcium chloride is used.

16. The process of claim 14, wherein sodium acetate or potassium acetate is used.

17. The process of claim 1, wherein said salt is used in an amount of from 0.5 to 20 times the molar amount of N-protected-L-aspartic anhydride.

18. The process of claim 1, wherein said salt is used in an amount of from 0.2 to 20 times the molar amount of L-phenylalanine.

19. The process of claim 17, wherein said salt is used in an amount of from 1 to 10 times the molar amount of N-protected-L-aspartic anhydride.

20. The process of claim 18, wherein said salt is used in an amount of from 1 to 10 times the molar amount of L-phenylalanine.

21. The process of claim 1, wherein said pH is adjusted by using an alkali metal hydroxide, an alkali metal carbonate, an alkaline earth metal hydroxide, an alkaline earth metal carbonate, or an organic amine.

* * * * *

UNITED STATES PATENT AND TRADEMARK OFFICE
CERTIFICATE OF CORRECTION

PATENT NO. : 4,740,616

DATED : April 26, 1988

INVENTOR(S) : TADASHI TAKEMOTO ET AL.

It is certified that error appears in the above-identified patent and that said Letters Patent is hereby corrected as shown below:

Column 2, line 16, replace "asparatic" with --aspartic--.

Column 3, line 1, replace "30°C" with -- -30°C--.

Column 3, line 2, replace "20°C" with -- -20°C--.

Column 3, line 45, replace "(High performance" with --(High Performance--.

Column 3, line 62, replace "the For-$\beta$-AP in a yield of 30.4%" with --the For-$\beta$-AP had been produced in a yield of 30.4%--.

Column 4, line 8, replace "For-$\beta$-AP in a yield" with --For-$\beta$-AP had been produced in a yield--.

Column 4, line 16, replace "while the For-$\beta$-AP in a yield of" with --while the For-$\beta$-AP was produced in a yield of--.

Column 5, line 44, replace "(0.006 mole)" with --(0.066 mole)--.

Column 6, line 54, replace "31 20°C" with -- -20°C--.

UNITED STATES PATENT AND TRADEMARK OFFICE
CERTIFICATE OF CORRECTION

PATENT NO. : 4,740,616

DATED : April 26, 1988

INVENTOR(S) : TADASHI TAKEMOTO ET AL.

It is certified that error appears in the above-identified patent and that said Letters Patent is hereby corrected as shown below:

Column 7, line 35, replace "was added thereto," with --was added thereto.--.

Column 8, line 59, replace "65.3%, based based on" with --65.3%, based on--.

Signed and Sealed this

Thirteenth Day of December, 1988

*Attest:*

DONALD J. QUIGG

*Attesting Officer*    *Commissioner of Patents and Trademarks*